US010857525B2

(12) United States Patent
Lim et al.

(10) Patent No.: US 10,857,525 B2
(45) Date of Patent: Dec. 8, 2020

(54) CATALYST FOR PREPARING ACROLEIN AND ACRYLIC ACID, AND PREPARATION METHOD THEREOF

(71) Applicant: LG CHEM, LTD., Seoul (KR)

(72) Inventors: Hyun-Sub Lim, Daejeon (KR); Duk-Ki Kim, Daejeon (KR); Hyun-Jong Shin, Daejeon (KR); Ju-Yeon Park, Daejeon (KR); Byung-Yul Choi, Daejeon (KR); Young-Hyun Choe, Daejeon (KR)

(73) Assignee: LG CHEM, LTD., Seoul (KR)

( * ) Notice: Subject to any disclaimer, the term of this patent is extended or adjusted under 35 U.S.C. 154(b) by 539 days.

(21) Appl. No.: 14/766,908

(22) PCT Filed: May 26, 2014

(86) PCT No.: PCT/KR2014/004671
§ 371 (c)(1),
(2) Date: Aug. 10, 2015

(87) PCT Pub. No.: WO2014/189342
PCT Pub. Date: Nov. 27, 2014

(65) Prior Publication Data
US 2016/0001270 A1 Jan. 7, 2016

(30) Foreign Application Priority Data

May 24, 2013 (KR) .................. 10-2013-0059092
May 23, 2014 (KR) .................. 10-2014-0062553

(51) Int. Cl.
*B01J 37/02* (2006.01)
*B01J 23/887* (2006.01)
*C07C 45/35* (2006.01)
*C07C 51/25* (2006.01)
*B01J 35/00* (2006.01)
*B01J 35/06* (2006.01)
*B01J 37/08* (2006.01)
*B01J 35/02* (2006.01)

(52) U.S. Cl.
CPC ......... *B01J 23/8876* (2013.01); *B01J 35/002* (2013.01); *B01J 35/023* (2013.01); *B01J 35/06* (2013.01); *B01J 37/0221* (2013.01); *B01J 37/08* (2013.01); *C07C 45/35* (2013.01); *C07C 51/252* (2013.01); *B01J 2523/00* (2013.01)

(58) Field of Classification Search
CPC ...... B01J 23/31; B01J 23/8876; B01J 35/023; B01J 37/0221; B01J 37/08; B01J 37/02; B01J 23/002; B01J 23/16; B01J 23/76; B01J 37/00; B01J 37/0223; B01J 2523/00; B01J 2523/13; B01J 2523/54; B01J 2523/68; B01J 2523/842; B01J 2523/845; C07C 45/35; C07C 47/22; C07C 57/104; C07C 51/252; C07C 45/22; C07C 45/00; C07C 45/37; C07C 47/37; C07C 57/04; C07C 51/16; C07C 51/25
See application file for complete search history.

(56) References Cited

U.S. PATENT DOCUMENTS

| | | | |
|---|---|---|---|
| 5,198,581 A | 3/1993 | Kawajiri et al. | |
| 5,532,199 A | 7/1996 | Watanabe et al. | |
| 6,784,134 B2 * | 8/2004 | Kasuga .................. | B01J 23/002 428/364 |
| 2004/0029724 A1 | 2/2004 | Seo et al. | |
| 2006/0161019 A1 | 7/2006 | Decourcy et al. | |
| 2013/0172615 A1 | 7/2013 | Kawano et al. | |

FOREIGN PATENT DOCUMENTS

| | | |
|---|---|---|
| EP | 0574895 A1 | 12/1993 |
| EP | 2617491 A1 | 7/2013 |
| JP | 63-200839 A | 8/1988 |
| JP | 64-63543 A | 3/1989 |
| JP | 05-049938 A | 3/1993 |
| JP | 06-000381 A | 1/1994 |
| JP | 10-28877 A | 2/1998 |
| JP | 10-168003 A | 6/1998 |
| JP | 2852712 B2 | 2/1999 |
| JP | 2002-273228 A | 9/2002 |
| JP | 2002-539100 A | 11/2002 |
| JP | 4119748 B2 | 7/2008 |
| JP | 2008-264766 A | 11/2008 |
| JP | 2010-077087 A | 4/2010 |
| JP | 2010-214217 A | 9/2010 |
| JP | 2010-235504 A | 10/2010 |
| JP | 2010-241700 A | 10/2010 |
| JP | 2010-248172 A | 11/2010 |
| JP | 2011-177616 A | 9/2011 |
| KR | 1991-0018335 A | 11/1991 |
| KR | 10-1997-0008964 B1 | 3/1999 |
| KR | 10-0204728 B1 | 3/1999 |
| KR | 10-0234874 B1 | 12/1999 |
| KR | 10-2007-0018578 A | 2/2007 |
| KR | 10-2002-0075281 B1 | 4/2007 |
| KR | 10-0709055 B1 | 4/2007 |
| KR | 10-2008-0010700 A | 1/2008 |
| KR | 10-2010-0134091 A | 12/2010 |
| KR | 10-2005-0115308 B1 | 1/2011 |

(Continued)

OTHER PUBLICATIONS

NPL: "Catalysts supported on alumina-silica glass fiber for neutralization of waste gases", Enviornmental engineering, 2011, pp. 85-89.*

(Continued)

*Primary Examiner* — Smita S Patel
(74) *Attorney, Agent, or Firm* — Dentons US LLP

(57) ABSTRACT

The present invention relates to a catalyst for preparing acrolein and acrylic acid, and a preparation method thereof. The catalyst according to the present invention can be uniformly packed in a reactor and the collapse of the catalyst can be minimized because it has excellent mechanical properties, and it can be stably used for a long period of time.

7 Claims, No Drawings

(56) References Cited

FOREIGN PATENT DOCUMENTS

| KR | 10-1011065 B1 | 1/2011 |
|---|---|---|
| WO | 2012/036038 A1 | 3/2012 |
| WO | 2012/073584 A1 | 6/2012 |

OTHER PUBLICATIONS

Federyaeva et al NPL:Catalysts supported on alumina-silica glass fiber for neturalization of waste gases, Enviornmental engeering, 2011, pp. 85-89.*

* cited by examiner

CATALYST FOR PREPARING ACROLEIN AND ACRYLIC ACID, AND PREPARATION METHOD THEREOF

This application is a National Stage Entry of International Application No. PCT/KR2014/004671, filed May 26, 2014, and claims the benefit of the priority to Korean Application No. 10-2013-0059092, filed May 24, 2013 and Korean Application No. 10-2014-0062553, filed May 23, 2014, all of which are incorporated by reference in their entirety for all purposes as if fully set forth herein.

TECHNICAL FIELD

The present invention relates to a supported catalyst for preparing acrolein and acrylic acid, and a preparation method thereof.

BACKGROUND OF ART

A method of carrying out vapor-phase oxidation of propylene, isobutylene, or tert-butanol and molecular oxygen in a multi-tubular fixed bed reactor including a catalyst layer is generally being used for preparing acrolein and/or acrylic acid.

However, said reaction is an exothermal reaction, and thus various methods of limiting the thickness of the catalyst layer or using a supported catalyst in which a catalytic active material is loaded are being applied in order to minimize the temperature rise during the reaction.

As it is known, the supported catalyst can be prepared by dispersing a catalytic active material or a catalyst precursor in a solvent so as to obtain a heterogeneous solution or slurry, spraying or impregnating the same to a supporting material, and heat-treating the same.

However, since the supported catalyst prepared by the method had a limit to the amount of the catalytic active material loaded therein, it was difficult to obtain sufficient catalytic activity. Accordingly, a method of adding a binder such as glycerin, ammonium nitrate, silica sol, polyvinyl alcohol, and so on for increasing the amount of the supported catalytic active material has been suggested. However, when the binder is used, there is a problem that the mechanical properties may decrease after heat treatment and thus the active ingredient is easily exfoliated during the packing process of the catalyst.

DETAILED DESCRIPTION OF THE INVENTION

Technical Problem

It is an aspect of the present invention to provide a catalyst for preparing acrolein and acrylic acid that has excellent mechanical properties, and in which collapse of the catalyst can be minimized in the process of using the same.

It is another aspect of the present invention to provide a preparation method of the catalyst.

Technical Solution

According to the present invention,
a catalyst for preparing acrolein and acrylic acid,
including an inert supporting material and a catalyst layer coated on the supporting material, wherein the catalyst layer includes a mixture of an catalytic active ingredient including at least molybdenum (Mo) and bismuth (Bi), and an inorganic fiber, and
satisfying the following Relational Equation, is provided.

$$0.1 \leq L/D \leq 0.2 \quad \text{[Relational Equation]}$$

In said Relational Equation, L is the number average length of the inorganic fiber, and D is the average thickness of the coated catalyst layer.

According to one embodiment of the present invention, the catalyst layer may include a catalytic active ingredient represented by the following Chemical Formula 1.

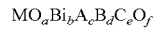  [Chemical Formula 1]

In Chemical Formula 1,
Mo is molybdenum; Bi is bismuth; A is one or more elements selected from the group consisting of Fe, Zn, Mn, Nb, and Te; B is one or more elements selected from the group consisting of Co, Rh, and Ni; C is one or more elements selected from the group consisting of Na, K, Li, Cs, Ta, Ca, Rb, and Mg; O is oxygen; and
a, b, c, d, e, and f are atomic ratios of each element, wherein b is 0.1 to 10, c is 0.1 to 10, d is 0.1 to 15, e is 0.001 to 10, and f is a number determined according to the oxidation state of each element, when a=12.

In addition, according to one embodiment of the present invention, the inorganic fiber may be one or more fibers selected from the group consisting of glass fiber, silica fiber, alumina fiber, and silica-alumina fiber. The inorganic fiber may have a number average length of 2 mm or less and a number average diameter of 2 to 40 μm. Further, the content of the inorganic fiber may be 2 to 15 parts by weight per 100 parts by weight of the active ingredient.

According to one embodiment of the present invention, the inert supporting material may be one or more materials selected from the group consisting of $SiO_2$, $Al_2O_3$, MgO, $MgCl_2$, $CaCl_2$, $ZrO_2$, $TiO_2$, $B_2O_3$, CaO, ZnO, BaO, $ThO_2$, $SiO_2$—$Al_2O_3$, $SiO_2$—MgO, $SiO_2$—$TiO_2$, $SiO_2$—$V_2O_5$, $SiO_2$—$CrO_2O_3$, $SiO_2$—$TiO_2$—MgO, and zeolite. The inert supporting material may have a number average diameter of 1 to 15 mm.

In addition, according to the present invention,
a preparation method of the catalyst for preparing acrolein and acrylic acid includes the steps of:
coating a powder including a catalytic active ingredient including at least molybdenum (Mo) and bismuth (Bi), and an inorganic fiber, on an inert supporting material; and
firing the coated inert supporting material.
Here, the firing step may be carried out under an oxygen atmosphere at 300 to 700° C. for 2 to 7 h.

Advantageous Effects

The catalyst for preparing acrolein and acrylic acid according to the present invention can be uniformly packed in a reactor and the collapse of the catalyst can be minimized because it has excellent mechanical properties, and it can be stably used for a long period of time.

DETAILED DESCRIPTION OF THE EMBODIMENTS

Hereinafter, the catalyst for preparing acrolein and acrylic acid according to the embodiments of the present invention and the preparation method thereof are explained.

Prior to this, technical terms used in in the present specification are only for mentioning specific embodiments and they are not intended to restrict the present invention. The singular expressions used here may include the plural expressions unless they are differently expressed contextually. The meaning of the term "include" or "comprise" used in the specification embodies specific characteristics, areas, essence, steps, actions, elements, or components, and does not exclude existence or addition of other specific characteristics, areas, essence, steps, actions, elements, or components.

In the process of researching the catalyst for preparing acrolein and acrylic acid, the present inventors recognized that prior supported catalysts had a limit in stable use because the catalytic active material was easily exfoliated in the process of transportation or packing, and differential pressure occurred by the collapse of the catalyst in the process of using the same because of their poor mechanical properties.

Therefore, the present inventors repeated studies for resolving the problem, and recognized that not only can the decrease in catalytic activity be minimized but also the active ingredient can be stably coated when the mixture of the catalytic active ingredient and the inorganic fiber is coated on the inert supporting material.

Particularly, the present inventors recognized that not only is more uniform packing possible but also the collapse of the catalyst can be prevented and it is possible to use the catalyst for a long period of time, because the mechanical properties of the catalyst are markedly improved by controlling the ratio of the number average length of the inorganic fiber to the thickness of the coated layer in the coating process.

According to one embodiment of the present invention,
a catalyst for preparing acrolein and acrylic acid,
including an inert supporting material and a catalyst layer coated on the supporting material, wherein the catalyst layer includes a mixture of an catalytic active ingredient including at least molybdenum (Mo) and bismuth (Bi), and an inorganic fiber, and
satisfying the following Relational Equation is provided.

$$0.1 \leq L/D \leq 0.2 \qquad \text{[Relational Equation]}$$

In said Relational Equation, L is the number average length of the inorganic fiber, and D is the average thickness of the coated catalyst layer.

The catalyst according to the present invention includes an inert supporting material and a catalyst layer coated on at least part of the supporting material.

The inert supporting material means the supporting material that does not show activity in the oxidation reaction for preparing acrolein and acrylic acid from propylene and so on.

The kind of the inert supporting material is not particularly limited, and common materials in the art to which the present invention pertains may be used. Preferably, the inert supporting material may be one or more materials selected from the group consisting of $SiO_2$, $Al_2O_3$, MgO, $MgCl_2$, $CaCl_2$, $ZrO_2$, $TiO_2$, $B_2O_3$, CaO, ZnO, BaO, $ThO_2$, $SiO_2$—$Al_2O_3$, $SiO_2$—MgO, $SiO_2$—$TiO_2$, $SiO_2$—$V_2O_5$, $SiO_2$—$CrO_2O_3$, $SiO_2$—$TiO_2$—MgO, and zeolite.

The shape of the inert supporting material may be a general sphere, and the number average diameter of the inert supporting material may be 1 to 15 mm, preferably 1 to 13 mm, and more preferably 1 to 10 mm. That is, the number average diameter of the inert supporting material may be preferably determined in the range disclosed above by considering the mechanical properties and the packing rate of the catalyst required to the present invention.

Meanwhile, the catalyst layer is coated on at least part of the inert supporting material. Particularly, the catalyst layer includes the mixture of the catalytic active ingredient and the inorganic fiber.

The catalyst may include a common component applied to the catalyst for preparing acrolein and acrylic acid as the active ingredient, and it is preferable for securing the catalytic activity to include at least molybdenum (Mo) and bismuth (Bi). More preferably, the catalyst layer may include the catalytic active ingredient represented by the following Chemical Formula 1.

$$Mo_aBi_bA_cB_dC_eO_f \qquad \text{[Chemical Formula 1]}$$

In Chemical Formula 1,
Mo is molybdenum; Bi is bismuth; A is one or more elements selected from the group consisting of Fe, Zn, Mn, Nb, and Te; B is one or more elements selected from the group consisting of Co, Rh, and Ni; C is one or more elements selected from the group consisting of Na, K, Li, Cs, Ta, Ca, Rb, and Mg; O is oxygen; and
a, b, c, d, e, and f are atomic ratios of each element, wherein b is 0.1 to 10, c is 0.1 to 10, d is 0.1 to 15, e is 0.001 to 10, and f is a number determined according to the oxidation state of each element, when a=12.

The catalytic active ingredient represented by Chemical Formula 1 can show excellent catalytic activity in the preparation of acrolein and acrylic acid, and thus makes it possible to provide more improved reaction activity.

Here, the volume portion of the catalytic active ingredient may be at least 40 volume %, preferably 60 to 90 volume %, based on the total volume of the catalyst according to the present invention. That is, when the volume of the inert supporting material and the inorganic fiber in the catalyst according to the present invention is over 60 volume %, it is not desirable because sufficient catalytic activity cannot be secured. Further, when the volume portion of the catalytic active ingredient is too high, it is also not desirable because the effect of improving the mechanical properties of the catalyst cannot be achieved.

Meanwhile, the catalyst layer includes the inorganic fiber in company with the catalytic active ingredient.

The inorganic fiber is coated (or supported) on the inert supporting material in a mixed state with the catalytic active ingredient, it allows the catalytic active material to be supported on the supporting material more stably, and it enables the improvement in the mechanical properties of the catalyst at the same time.

Particularly, the catalyst according to the present invention satisfies the following Relational Equation.

$$0.1 \leq L/D \leq 0.2 \qquad \text{[Relational Equation]}$$

In said Relational Equation, L is the number average length of the inorganic fiber, and D is the average thickness of the coated catalyst layer.

That is, the catalyst according to the present invention is prepared so that the ratio of the average thickness (D) of the catalyst layer coated on the inert supporting material and the number average length (L) of the inorganic fiber included in the catalyst layer satisfies said Relational Equation. Accordingly, the catalyst according to the present invention can exhibit apparently improved mechanical properties in comparison to the supported catalysts which do not include the inorganic fiber in the catalyst layer or do not satisfy said Relational Equation.

The catalytic active ingredient may be supported somewhat on the inert supporting material even when L/D is below 0.1 or over 0.2 in said Relational Equation. However, when L/D is less than 0.1, it is not preferable because the overall mechanical properties of the catalyst may decrease, for example, the attrition rate of the catalyst increases and the shatter strength decreases. In addition, when LID is larger than 0.2, it is not preferable because the mechanical properties of the catalyst may decrease somewhat and the oxidation reaction yield may decrease because of the decrease of the catalytic active ingredient.

According to the present invention, L/D may be determined by totally considering the kind and diameter of the inert supporting material, the thickness of the catalyst layer to be formed, the kind and content of the catalytic active ingredient included in the catalyst layer, the content of the inorganic fiber, the material and length of the inorganic fiber, and so on.

As a non-restrictive example, the number average length (L) of the inorganic fiber may be 2 mm or less, or 0.05 to 2 mm, or 0.1 to 1.5 mm, or 0.1 to 1 mm to be uniformly mixed with the catalytic active ingredient. Further, the number average diameter of the inorganic fiber may be 2 to 40 μm, or 2 to 30 μm, or 4 to 20 μm, and the average thickness (D) of the catalyst layer may be determined by considering said Relational Equation.

In the present invention, the material of the inorganic fiber is not particularly limited, and common fibers in the art to which the present invention pertains can be used. For example, in order to sufficiently realize said effects without a negative influence on the catalytic activity, it is preferable that the inorganic fiber is one or more fibers selected from the group consisting of glass fiber, silica fiber, alumina fiber, and silica-alumina fiber.

The content of the inorganic fiber included in the catalyst according to the present invention may be determined in the range in which said effect according to adding the inorganic fiber can be sufficiently exhibited and the catalytic activity does not decrease. As a non-restrictive example, the content of the inorganic fiber may be 2 to 15 parts by weight, preferably 2 to 10 parts by weight, per 100 parts by weight of the catalytic active ingredient.

According to another embodiment of the present invention, a preparation method of the catalyst for preparing acrolein and acrylic acid including the steps of coating a powder including a catalytic active ingredient including at least molybdenum (Mo) and bismuth (Bi), and an inorganic fiber, on an inert supporting material, and firing the coated inert supporting material, is provided.

As a method of loading the mixture of the catalytic active ingredient and the inorganic fiber on the surface of the spherical inert supporting material, the method according to said embodiment uses a coating method instead of a impregnating method, and the number average length of the inorganic fiber and the average thickness of the catalyst layer may be controlled to satisfy said Relational Equation.

Here, the mixture of the catalytic active ingredient and the inorganic fiber has a powdery form. Therefore, as the method of coating the powder on the inert supporting material, a method of putting the inert supporting material and the powder in a centrifugal rotary machine or an oscillating granulator and agitating the same may be used. At this time, a solvent such as water, alcohols, or a mixed solution of water and alcohols may be slightly added thereto to induce smooth coating.

Furthermore, as the coating method of the powder on the inert supporting material, a method of immersing the inert supporting material in a slurry including the powder, or a method of spraying the slurry on the inert supporting material, may be used. However, the methods using the slurry may decrease the overall productivity because they need a longer drying time after the coating process than the method using the powder, and the spraying nozzle may be clogged with the inorganic fiber in the process of spraying the slurry.

The coating step may be carried out at room temperature, and the number average length (L) of the inorganic fiber and the average thickness (D) of the catalyst layer may be controlled in the coating step to satisfy said Relational Equation. In addition, the coating step may be carried out by totally considering the number average diameter of the inert supporting material, the kind and content ratio of the catalytic active ingredient and the inorganic fiber, the volume portion of the catalytic active ingredient in the whole catalyst, and so on.

The coated inert supporting material may be prepared into the catalyst for preparing acrolein and acrylic acid according to the present invention through a drying and firing step.

The drying of the coated inert supporting material is a process for drying the solvent used in the coating step, and as a non-restrictive example, it may be carried out at a temperature of 90 to 200° C. for 2 to 24 h. Further, it is advantageous in the aspect of sufficient exhibition of the catalytic activity to carry out the firing step under an oxygen atmosphere at 300 to 700° C. for 2 to 7 h.

The catalyst prepared in this way can show excellent activity in a catalytic vapor-phase oxidation reaction for obtaining acrolein and acrylic acid from propylene, isobutylene, or tert-butanol. The catalytic vapor-phase oxidation reaction may be carried out by using a multi-tubular fixed bed reactor packed with the catalyst (as a non-restrictive example, a multi-tubular fixed bed reactor equipped with a shell and tube type of heat exchanger). The mole ratio of the raw materials and oxygen put in the reactor may be 1:0.5 to 1:3, and the reaction may be carried out at 200 to 450° C. under a pressure of 0.1 to 10 atm.

Hereinafter, preferable examples and comparative examples are presented for better understanding of the present invention. However, the following examples are only for illustrating the present invention and the present invention is not limited to or by them.

Preparation Example

Preparation of Catalytic Active Ingredient

A $1^{st}$ solution was prepared by dissolving about 1000 g of ammonium molybdate in about 2500 ml of distilled water in a 5 L glass reactor equipped with a stirrer while heating the same to about 90° C.

Separately, a $2^{nd}$ solution was prepared by dissolving about 84 g of nitric acid in about 500 ml of distilled water while adding about 503.73 g of bismuth nitrate, about 267 g of iron nitrate, about 755.54 g of cobalt nitrate, and about 19.09 g of potassium nitrate thereto and mixing the same.

A suspension was prepared by mixing the $1^{st}$ solution and the $2^{nd}$ solution while maintaining the temperature at about 40° C. After drying the prepared suspension in an electric oven at about 130° C. for about 24 h, a powdery material was obtained by pulverizing the dried material to a diameter of about 130 μm or less while stirring for about 2 h.

Example 1

A mixture including 5 parts by weight of silica-alumina fiber (number average diameter: about 10 μm, number average length: about 120 μm) per 100 parts by weight of the catalytic active ingredient according to Preparation Example was prepared.

After putting about 500 g of alumina balls having a number average diameter of about 2.8 mm in a centrifugal rotary machine, the coating step was carried out while adding the mixture of the catalytic active ingredient and the silica-alumina fiber and water thereto several times. The catalyst was obtained by drying the coated alumina balls at about 130° C. for about 12 h and firing the same under an oxygen atmosphere at about 500° C. for about 5 h. The composition ratio of the elements except oxygen in the catalytic active ingredient was recognized as $Mo_{12}Bi_{2.2}Fe_{1.4}Co_{5.5}K_{0.4}$.

The average thickness of the coated catalyst layer of the catalyst was about 1.2 mm (L/D according to Relational Equation was about 0.1), and the amount of the loaded catalytic active material [=(weight of the catalytic active material coated)/(weight of the supporting material used)*100] was about 250%.

Example 2

A mixture including 5 parts by weight of silica-alumina fiber (number average diameter: about 10 μm, number average length: about 140 μm) per 100 parts by weight of the catalytic active ingredient according to Preparation Example was prepared. The catalyst was obtained by the same method as in Example 1, except that the coating number of the mixture of the catalytic active ingredient and the silica-alumina fiber on the alumina balls in the coating step was controlled so that the average thickness of the coated catalyst layer of the final catalyst was about 1.2 mm (L/D according to Relational Equation was about 0.12).

Example 3

A mixture including 5 parts by weight of silica-alumina fiber (number average diameter: about 10 μm, number average length: about 180 μm) per 100 parts by weight of the catalytic active ingredient according to Preparation Example was prepared. The catalyst was obtained by the same method as in Example 1, except that the coating number of the mixture of the catalytic active ingredient and the silica-alumina fiber on the alumina balls in the coating step was controlled so that the average thickness of the coated catalyst layer of the final catalyst was about 1.2 mm (L/D according to Relational Equation was about 0.15).

Example 4

A mixture including 5 parts by weight of silica-alumina fiber (number average diameter: about 10 μm, number average length: about 220 μm) per 100 parts by weight of the catalytic active ingredient according to Preparation Example was prepared. The catalyst was obtained by the same method as in Example 1, except that the coating number of the mixture of the catalytic active ingredient and the silica-alumina fiber on the alumina balls in the coating step was controlled so that the average thickness of the coated catalyst layer of the final catalyst was about 1.2 mm (L/D according to Relational Equation was about 0.18).

Example 5

A mixture including 5 parts by weight of silica-alumina fiber (number average diameter: about 10 μm, number average length: about 240 μm) per 100 parts by weight of the catalytic active ingredient according to Preparation Example was prepared. The catalyst was obtained by the same method as in Example 1, except that the coating number of the mixture of the catalytic active ingredient and the silica-alumina fiber on the alumina balls in the coating step was controlled so that the average thickness of the coated catalyst layer of the final catalyst was about 1.2 mm (L/D according to Relational Equation was about 0.2).

Comparative Example 1

A mixture including 5 parts by weight of silica-alumina fiber (number average diameter: about 10 μm, number average length: about 84 μm) per 100 parts by weight of the catalytic active ingredient according to Preparation Example was prepared. The catalyst was obtained by the same method as in Example 1, except that the coating number of the mixture of the catalytic active ingredient and the silica-alumina fiber on the alumina balls in the coating step was controlled so that the average thickness of the coated catalyst layer of the final catalyst was about 1.2 mm (L/D according to Relational Equation was about 0.07).

Comparative Example 2

A mixture including 5 parts by weight of silica-alumina fiber (number average diameter: about 10 μm, number average length: about 300 μm) per 100 parts by weight of the catalytic active ingredient according to Preparation Example was prepared. The catalyst was obtained by the same method as in Example 1, except that the coating number of the mixture of the catalytic active ingredient and the silica-alumina fiber on the alumina balls in the coating step was controlled so that the average thickness of the coated catalyst layer of the final catalyst was about 1.2 mm (L/D according to Relational Equation was about 0.25).

Comparative Example 3

A mixture including 5 parts by weight of silica-alumina fiber (number average diameter: about 10 μm, number average length: about 360 μm) per 100 parts by weight of the catalytic active ingredient according to Preparation Example was prepared. The catalyst was obtained by the same method as in Example 1, except that the coating number of the mixture of the catalytic active ingredient and the silica-alumina fiber on the alumina balls in the coating step was controlled so that the average thickness of the coated catalyst layer of the final catalyst was about 1.2 mm (L/D according to Relational Equation was about 0.3).

Comparative Example 4

A mixture including 5 parts by weight of silica-alumina fiber (number average diameter: about 10 μm, number average length: about 480 μm) per 100 parts by weight of the catalytic active ingredient according to Preparation Example was prepared. The catalyst was obtained by the same method as in Example 1, except that the coating number of the mixture of the catalytic active ingredient and the silica-alumina fiber on the alumina balls in the coating step was controlled so that the average thickness of the coated catalyst layer of the final catalyst was about 1.2 mm (L/D according to Relational Equation was about 0.4).

Comparative Example 5

The catalyst was obtained by the same method as in Example 1, except that the catalytic active ingredient was coated on the alumina balls without adding the silica-alumina fiber thereto.

Comparative Example 6

The cylinder form catalyst was obtained by extruding the pulverized powdery material obtained after drying the suspension in Preparation Example into a cylinder form having about 5 mm external diameter and about 5.5 mm length, and firing the same under an air atmosphere of about 500° C. for about 5 h.

Experimental Example 1

Measurements on Mechanical Properties of the Catalyst

Strength, attrition rate, and shatter strength were measured for each catalyst according to the examples and comparative examples by the following methods, and the results are listed in the following Table 1.

1) Impact Strength ($kgf/cm^2$): measured by using a grain crushing strength tester (model name: GCS Tester (ASTM D-4179 & D-6175), manufacturer: VINCI Technologies).

2) Attrition Rate (%): measured with a 30 rpm condition for 30 min by using an attrition tester (model name: Rotating Drum Attrition Tester (ASTM D-4058-96), manufacturer: VINCI Technologies).

3) Shatter Strength (%): after covering the bottom of a 6000 mm diameter reaction tube with a 2 mm mesh, 100 g of the catalyst was dropped into the reaction tube, and then sieved by using a 3.5 mm mesh. The weight of the catalyst left on the 3.5 mm mesh was measured and the shatter strength was calculated according to the following equation.

Shatter Strength=[(Weight of the catalyst left on the mesh)/(Weight of the dropped catalyst)*100]

TABLE 1

| | Shape | L/D | Impact Strength ($kgf/cm^2$) | Attrition Rate (%) | Shatter Strength (%) |
|---|---|---|---|---|---|
| Example 1 | Sphere | 0.1 | 10.1 | 3.0 | 99.3 |
| Example 2 | Sphere | 0.12 | 10.3 | 2.8 | 99.6 |
| Example 3 | Sphere | 0.15 | 10.8 | 2.2 | 99.3 |
| Example 4 | Sphere | 0.18 | 11 | 2.4 | 99.3 |
| Example 5 | Sphere | 0.2 | 10.5 | 2.8 | 99.2 |
| Comparative Example 1 | Sphere | 0.07 | 9.2 | 3.6 | 99.1 |
| Comparative Example 2 | Sphere | 0.25 | 9.9 | 3.1 | 98.5 |
| Comparative Example 3 | Sphere | 0.3 | 10.1 | 3.2 | 98.8 |
| Comparative Example 4 | Sphere | 0.4 | 9.8 | 3.4 | 98.9 |
| Comparative Example 5 | Sphere | — | 5.7 | 5.8 | 87.8 |
| Comparative Example 6 | Cylinder | — | 3.2 | 12 | 85.1 |

Experimental Example 2

Measurement on Activity of the Catalyst

Acrolein and acrylic acid were prepared by a catalytic vapor-phase oxidation reaction of propylene, a raw material, in the presence of each catalyst according to the examples and comparative examples. The reaction was carried out in a multi-tubular fixed bed reactor equipped with a shell and tube type of heat exchanger (internal diameter of tube: 1 inch (25.4 mm), diameter of shell: 350 mm, length of catalyst-packing section: 3000 mm), and the reaction was carried out at a reaction temperature of about 305° C. while streaming the raw material mixture gas (propylene: 8 volume %, oxygen: 14 volume %, water vapor: 18 volume %, inert gas: 60 volume %) with a space velocity of 1500 $h^{-1}$.

The conversion rate of propylene, the selectivity of acrolein, and the yield were calculated by the following equations and the results are listed in the following Table 2.

Conversion rate of propylene (%)=[(mole of propylene reacted)/(mole of propylene provided)]*100    1)

Selectivity of acrolein(%)=[(mole of acrolein produced)/(mole of propylene reacted)]*100    2)

Yield(%)=[(mole of acrolein and acrylic acid produced)/(mole of propylene provided)]*100    3)

TABLE 2

| Catalyst | Conversion Rate of Propylene (%) | Selectivity of Acrolein (%) | Yield (%) |
|---|---|---|---|
| Example 1 | 98.3 | 94.1 | 92.5 |
| Example 2 | 98.6 | 94.3 | 92.9 |
| Example 3 | 98.4 | 94.3 | 92.8 |
| Example 4 | 98.3 | 94.5 | 92.9 |
| Example 5 | 98.4 | 94.1 | 92.6 |
| Comparative Example 1 | 98.1 | 93.9 | 92.1 |
| Comparative Example 2 | 98.1 | 94.1 | 92.3 |
| Comparative Example 3 | 98.2 | 94.0 | 92.3 |
| Comparative Example 4 | 98.0 | 94.0 | 92.1 |
| Comparative Example 5 | 98.2 | 93.6 | 91.9 |
| Comparative Example 6 | 98.3 | 92.0 | 90.4 |

As shown in Tables 1 and 2, it is recognized that the catalysts according to the examples are superior to the catalysts according to the comparative examples not only in the catalytic activity but also in the mechanical properties such as impact strength, attrition rate, shatter strength, and so on.

The invention claimed is:

1. A catalyst for preparing acrolein and acrylic acid, including an inert supporting material and a catalyst layer coated on the supporting material, wherein the catalyst layer includes a mixture of a catalytic active ingredient including at least molybdenum (Mo) and bismuth (Bi), and an inorganic fiber, and satisfying the following Relational Equation:

$0.1 \leq L/D \leq 0.2$    [Relational Equation]

wherein, in said Relational Equation, L is the number average length of the inorganic fiber, and D is the average thickness of the coated catalyst layer, and wherein the inorganic fiber is silica-alumina fiber, wherein the catalytic active ingredient is represented by the following Chemical Formula 1:

$Mo_aBi_bA_cB_dC_eO_f$    [Chemical Formula 1]

wherein in Chemical Formula 1,

Mo is molybdenum; Bi is bismuth; A is one or more elements selected from the group consisting of Fe, Zn, Mn, Nb, and Te; B is one or more elements selected from the group consisting of Co, Rh, and Ni; C is one or more elements selected from the group consisting of Na, K, Li, Cs, Ta, Ca, Rb, and Mg; O is oxygen; and a, b, c, d, e, and f are atomic ratios of each element, wherein b is 0.1 to 10, c is 0.1 to 10, d is 0.1 to 15, e is 0.001 to 10, and f is a number determined according to the oxidation state of each element, when a=12.

2. The catalyst according to claim 1, wherein the inorganic fiber has a number average length of 2 mm or less and a number average diameter of 2 to 40 μm.

3. The catalyst according to claim 1, wherein the content of the inorganic fiber is 2 to 15 parts by weight per 100 parts by weight of the catalytic active ingredient.

4. The catalyst according to claim 1, wherein the inert supporting material is one or more materials selected from the group consisting of $SiO_2$, $Al_2O_3$, MgO, $MgCl_2$, $CaCl_2$, $ZrO_2$, $TiO_2$, $B_2O_3$, CaO, ZnO, BaO, $ThO_2$, $SiO_2$—$Al_2O_3$, $SiO_2$—MgO, $SiO_2$—$TiO_2$, $SiO_2$—$V_{205}$, $SiO_2$—$CrO_2O_3$, $SiO_2$—$TiO_2$—MgO, and zeolite.

5. The catalyst according to claim 1, wherein the inert supporting material has a number average diameter of 1 to 15 mm.

6. A preparation method of the catalyst for preparing acrolein and acrylic acid according to claim 1, including:
coating a powder including a catalytic active ingredient including at least molybdenum (Mo) and bismuth (Bi), and an inorganic fiber, on an inert supporting material; and
firing the coated inert supporting material.

7. The preparation method according to claim 6, wherein the firing is carried out under an oxygen atmosphere of 300 to 700° C. for 2 to 7 h.

* * * * *